(12) United States Patent
Rogachefsky (10) Patent No.: US 10,335,282 B2
(45) Date of Patent: Jul. 2, 2019

(54) MAGNETIC JOINT REPLACEMENT (71) Applicant: Richard A. Rogachefsky, San Pedro, CA (US)

(72) Inventor: Richard A. Rogachefsky, San Pedro, CA (US)

(73) Assignee: Richard A. Rogachefsky, San Pedro, CA (US)

( * ) Notice: Subject to any disclaimer, the term of this patent is extended or adjusted under 35 U.S.C. 154(b) by 0 days.

(21) Appl. No.: 15/019,343

(22) Filed: Feb. 9, 2016

(65) Prior Publication Data

US 2017/0224495 A1 Aug. 10, 2017

(51) Int. Cl.
*A61F 2/32* (2006.01)
*A61F 2/34* (2006.01)
*A61F 2/36* (2006.01)
*A61F 2/30* (2006.01)
*A61F 2/40* (2006.01)

(52) U.S. Cl.
CPC .......... *A61F 2/34* (2013.01); *A61F 2/30* (2013.01); *A61F 2/36* (2013.01); *A61F 2/40* (2013.01); *A61F 2002/30079* (2013.01)

(58) Field of Classification Search
CPC ............ A61F 2002/30054; A61F 2002/30079
See application file for complete search history.

(56) References Cited

U.S. PATENT DOCUMENTS 3,745,995 A 7/1973 Kraus
3,820,534 A 6/1974 Kraus
(Continued)

FOREIGN PATENT DOCUMENTS

DE 4343117 6/1995
DE 19963908 7/2001
(Continued)

OTHER PUBLICATIONS

Gonzalez et al.: Intramedullary Fixation of Metacarpal and Proximal Phalangeal Fractures of the Hand; Clinical Orthopaedics and Related Research, No. 327, pp. 47-54 (Lippincott-Raven 1996).
(Continued)

*Primary Examiner* — Christopher D. Prone
(74) *Attorney, Agent, or Firm* — Knobbe, Martens, Olson & Bear, LLP (57) ABSTRACT

A joint prosthesis includes first and second articulated corresponding joint components implantable within a body of a patient, wherein the corresponding joint components have corresponding surfaces that are relatively displaceable with respect to each other over a predefined functional range of motion of the corresponding joint components. The corresponding joint components each comprise one or more magnetic elements creating gradient magnetic fields having relatively strongest and weakest field areas over different portions of each of the corresponding surfaces, wherein the gradient magnetic fields are strongest in attraction at positions of the corresponding surfaces which align when the corresponding surfaces are at a boundary of the predefined functional range of motion, and deter joint dislocation by deterring relative movement of the corresponding surfaces beyond the boundary.

13 Claims, 2 Drawing Sheets

(56) References Cited

U.S. PATENT DOCUMENTS

| | | | |
|---|---|---|---|
| 4,024,588 A * | 5/1977 | Janssen | A61F 2/30 623/18.12 |
| 4,164,793 A | 8/1979 | Swanson | |
| 4,198,712 A | 4/1980 | Swanson | |
| 4,216,548 A | 8/1980 | Kraus | |
| 4,266,532 A | 5/1981 | Ryaby et al. | |
| 4,332,037 A | 6/1982 | Esformes et al. | |
| 4,587,956 A | 5/1986 | Griffin et al. | |
| 4,913,137 A | 4/1990 | Azer et al. | |
| 4,936,860 A | 6/1990 | Swanson | |
| 4,942,884 A | 7/1990 | Ichinomiya et al. | |
| 5,066,296 A | 11/1991 | Chapman et al. | |
| 5,281,224 A | 1/1994 | Faccioli et al. | |
| 5,518,495 A | 5/1996 | Kolt | |
| 5,720,046 A | 2/1998 | Lopez et al. | |
| 5,782,743 A | 7/1998 | Russell | |
| 5,879,386 A | 3/1999 | Jore | |
| 5,888,203 A | 3/1999 | Goldberg | |
| 6,146,324 A | 11/2000 | Engel | |
| 6,245,109 B1 | 6/2001 | Mendes et al. | |
| 6,317,630 B1 | 11/2001 | Gross et al. | |
| 6,322,562 B1 | 11/2001 | Wolter | |
| 6,344,021 B1 | 2/2002 | Juster et al. | |
| 6,533,788 B1 | 3/2003 | Orbay | |
| 6,716,249 B2 | 4/2004 | Hyde | |
| 6,778,861 B1 | 8/2004 | Liebrecht et al. | |
| 6,932,818 B2 | 8/2005 | Behrens | |
| 8,157,803 B1 | 4/2012 | Zirkle, Jr. et al. | |
| 8,801,796 B2 | 8/2014 | Rogachefsky | |
| 8,961,615 B2 | 2/2015 | Rogachefsky | |
| 9,227,080 B2 | 1/2016 | Rogachefsky | |
| 9,421,049 B2 | 8/2016 | Rogachefsky | |
| 9,687,351 B2 | 6/2017 | Rogachefsky | |
| 2002/0111690 A1 | 8/2002 | Hyde | |
| 2002/0128651 A1 | 9/2002 | Hyde, Jr. | |
| 2003/0073999 A1 | 4/2003 | Putnam | |
| 2003/0083661 A1 | 5/2003 | Orbay et al. | |
| 2003/0158585 A1 | 8/2003 | Burnett | |
| 2003/0236572 A1 | 12/2003 | Bertram, III | |
| 2004/0138663 A1 | 7/2004 | Kosashvili et al. | |
| 2004/0138754 A1 | 7/2004 | Lang et al. | |
| 2004/0176803 A1 | 9/2004 | Whelan et al. | |
| 2004/0176805 A1 | 9/2004 | Whelan et al. | |
| 2005/0070916 A1 | 3/2005 | Hollstien et al. | |
| 2005/0075562 A1 | 4/2005 | Szakelyhidi, Jr. et al. | |
| 2005/0288744 A1 | 12/2005 | Pilla et al. | |
| 2006/0079897 A1 | 4/2006 | Harrison et al. | |
| 2006/0142865 A1 | 6/2006 | Hyde, Jr. | |
| 2006/0149386 A1 * | 7/2006 | Clarke | A61F 2/32 623/18.12 |
| 2007/0100457 A1 | 5/2007 | Hyde, Jr. | |
| 2007/0265628 A1 | 11/2007 | Kraus et al. | |
| 2008/0051621 A1 | 2/2008 | Vines et al. | |
| 2008/0255556 A1 | 10/2008 | Berger | |
| 2008/0294163 A1 | 11/2008 | Chou et al. | |
| 2008/0306324 A1 | 12/2008 | Bonutti et al. | |
| 2009/0082610 A1 | 3/2009 | Wolf et al. | |
| 2009/0099404 A1 | 4/2009 | Kraus et al. | |
| 2010/0036493 A1 | 2/2010 | Simon | |
| 2010/0131024 A1 | 5/2010 | Lathrop et al. | |
| 2010/0145337 A1 | 6/2010 | Janna et al. | |
| 2010/0145464 A1 | 6/2010 | Sidhom | |
| 2010/0222631 A1 | 9/2010 | Pilla | |
| 2010/0249938 A1 | 9/2010 | Gunther et al. | |
| 2010/0331993 A1 | 12/2010 | Gradl | |
| 2011/0066245 A1 | 3/2011 | Lang et al. | |
| 2011/0112352 A1 | 5/2011 | Pilla et al. | |
| 2011/0130618 A1 | 6/2011 | Ron Edoute et al. | |
| 2011/0207989 A1 | 8/2011 | Pilla et al. | |
| 2011/0213195 A1 | 9/2011 | Kraus et al. | |
| 2011/0218381 A1 | 9/2011 | Ruohonen | |
| 2011/0230943 A1 | 9/2011 | Johnson et al. | |
| 2011/0257754 A1 | 10/2011 | Fleischmann | |
| 2012/0302821 A1 | 11/2012 | Burnett | |
| 2015/0005886 A1 | 1/2015 | Pinneo | |
| 2015/0080636 A1 | 3/2015 | Rogachefsky et al. | |
| 2017/0312083 A1 | 11/2017 | Rogachefsky | |

FOREIGN PATENT DOCUMENTS

| | | |
|---|---|---|
| EP | 0501048 | 9/1992 |
| EP | 2797525 | 11/2014 |
| GB | 1466337 | 3/1977 |
| JP | 2007-283110 | 11/2007 |
| JP | 2011-507643 | 3/2011 |
| JP | 6184975 | 8/2017 |
| JP | 2017-205561 | 11/2017 |
| WO | WO 2011/051947 | 5/2011 |
| WO | WO 2013/101962 | 7/2013 |
| WO | WO 2013/181144 | 12/2013 |
| WO | WO 2014/106170 | 7/2014 |
| WO | WO 2015/035194 | 3/2015 |

OTHER PUBLICATIONS

Markov, "Biological Windows": A Tribute to W. Ross Adey, The Environmentalist 25, p. 67-74, 2005, 2005 Springer Science + Business Media, Inc.

Orbay et al.: The Treatment of Unstable Metacarpal and Phalangeal Shaft Fractures with Flexible Nonlocking and Locking Intramedullary Nails; Hand Clin 22, pp. 297-286 (Elsevier Saunders 2006).

Orbay: Intramedullary Nailing of Metacarpal Shaft Fractures; Techniques in Hand and Upper Extremity Surgery, vol. 9, Issue 2, pp. 69-73 (Lippincott Williams & Wilkins 2005).

Stryker: VariAx Distal Radius Locking Plate System, Operative Technique, Literature No. 90-07799 (Stryker 2008).

\* cited by examiner

MAGNETIC JOINT REPLACEMENT

FIELD OF THE INVENTION

This disclosure relates generally to joint replacements. More specifically, this disclosure relates to replacing a joint with components comprising magnets creating a varying magnetic field which decreases the probability of dislocation in the replaced joint.

BACKGROUND

Normal Joint Function

The anatomy of the normal joint demonstrates articular cartilage on subchondral bone. The two cartilage surfaces oppose each other. The synovial tissue around the joint produces joint fluid, which lubricates the joint and nourishes the cartilage.

The ligaments that surround the joints provide stability to the joints. Normal joint motion occurs when the two cartilage surfaces glide across each other in both rotation and translation. The cartilage is made up of chondrocytes, which are the cartilage cells and extracellular matrix. The extracellular matrix is composed of type 2 collagen and proteoglycans. Proteoglycans are large sulfated sugar molecules. Both components are produced by the chondrocytes. The function of these large proteoglycan molecules is that they attract water molecules through their negatively charged sulfur ions, which attract the positive hydrogen atom of the water dipole. The collagen gives the cartilage tensile strength which resists shear forces. The proteoglycans allow cartilage to absorb water by ionic attraction and osmotic gradients. Cartilage also imbibes water through flexion and extension of the joint. As a result, cartilage is a highly specialized tissue with characteristics to absorb compressive forces and resist tensile forces. The subchondral bone provides support to the articular cartilage and blood supply to the deeper cartilage layers. Histologically, articular cartilage has 4 layers: superficial layer, transitional layer, radial layer and calcified layer. Each layer has a characteristic morphology and function. (Ref 1).

Pathological Degenerative Arthritis

When the articular cartilage structure is maintained normal joint function occurs. When the articular cartilage degenerates joint function is compromised. The stages of degeneration are initiated by an insult such as a traumatic event or through gradual degeneration and mechanical wear over time. Biochemically the initiating factors are the release of chemotactic factors by the chondrocytes and synovial tissue such as IL-1, and TNF, which attract white blood cells such as leukocytes and macrophages into the region. These white blood cells release enzymes such as metalloproteinases which degrade collagen and proteoglycans. (Ref. 1, Ref. 2). In addition, chondrocytes release these degradative enzymes into the extracellular matrix further degrading the cartilage. As the proteoglycans break down, the cartilage has less ability to hold water. As a result, the cartilage has less ability to resist compressive forces. As the collagen gets degraded, the cartilage has decreased ability to resist tensile forces. As the process progresses, increased degradation and mechanical wear of the articular cartilage occurs resulting in degenerative osteoarthritis. (Ref. 1, Ref 2) The cartilage surface becomes thinner until there is bone on bone contact. During the degenerative process the synovial fluid becomes thinner and the bone edges of the joint form osteophytes in an attempt to stabilize the joint. As the joint continues to deteriorate, the patient clinically has increased swelling, pain, loss of motion and loss of function.

Many musculoskeletal diseases lead to joint damage and degenerative arthritis such as trauma and fractures that heal malaligned, infection that damages the joint surface, inflammatory arthritis such as rheumatoid arthritis that has hypertrophic synovium that damages the cartilage surface. (Ref. 1).

Treatment options for degenerative osteoarthritis range from conservative to surgical depending on the disease severity. Conservative treatment includes rest, NSAID, braces etc. Hyaluronic gel injections provide good relief of symptoms for significant period of time by replacing the thin synovial fluid with hyaluronic gel that is similar in viscosity to normal synovial fluid. The gel lubricates the joint and provides an anti-inflammatory effect. If conservative treatment fails and the patient becomes increasingly symptomatic, then surgical treatment is instituted. Surgical options include arthroscopy and debridement, open debridement, osteotomy, arthrodesis and joint replacement arthroplasty. (Ref. 3). Arthroscopy and joint debridement are indicated for early degenerative arthritis. Arthrodesis is for more advanced degeneration. The purpose of arthrodesis surgery is to remove the involved degenerative joint surfaces. Then the joint is made stiff by bridging the 2 bone ends together with internal fixation such as plate and screws or external fixation. This eliminates motion and providing a stable joint region. As a result, pain is removed and function is improved. (Ref 4). Fusion can be done for any arthritic joint and common joints that are fused are spine vertebral joint segments, ankle and feet, wrist and hands, etc. (Ref. 5)

The disadvantages of arthrodesis surgery are that motion is lost in the fused joint. A joint can take from 2-4 months to heal. In addition complications of arthrodesis are nonunion, or implant failure. (Ref 4). Arthrodesis of spinal segments can be especially problematic and even with newer instrumentation, fusion failure occurs. Also, once the joint is fused stiff there is no motion and the stress is transferred to adjacent joints, and these joints may eventually deteriorate.

The most common surgical treatment for degenerative arthritis of joints is joint arthroplasty or joint replacement. (Ref 6, Ref. 7, Ref. 8). The most common joint replacements performed are total hip and total knee replacements. Other joint replacements performed are finger joint replacements, elbow joint replacements, wrist replacements and shoulder replacements. (Ref. 5, Ref. 9, Ref. 10, Ref. 11). The introduction and refinement of total joint replacements has been one of the great advances in orthopedic surgery. (Ref. 8). The advantages of total joint replacements are that an arthritic joint that has poor motion and function and which causes significant pain and discomfort can be replaced with metal and polyethylene, eliminating pain and increasing motion and function. Total hip replacements have been performed extensively to replace degenerated hips. They have been widely successful eliminating pain and increasing function. The life span for a total hip replacement can average between 20-30 years. (Ref. 6, Ref 7, Ref. 8).

Total hip replacements are placed by removing the arthritic femoral head and placing a metallic or ceramic femoral component which has a head portion and a stem portion that is fixated into the femoral canal by press or interference fit or with cement. The degenerated acetabulum is removed and a metal or ceramic cup or socket is placed into the acetabulum and fixated by press or interference fit or stabilized with cement or screws. A polyethylene liner is placed in the cup as the articulating surface for the head of the femoral component. Once the components are in place the femoral component is reduced into the acetabular component. Stability of the prosthesis through a range of motion is obtained by the congruent fit of the head portion of the femoral component and the cup component of the acetabulum, the correct alignment and positioning of the components, and the tension obtained of the soft tissues such as the muscles, ligaments and tendons around the components. (Ref 8, Ref 12).

Most total hip replacements are placed using a posterior approach from the back of the hip. This approach is more commonly used due to the fact that visualization of the hip is improved. Going posteriorly, however, has a higher dislocation rate (Ref 12, Ref. 13), as this approach results in the posterior capsule or ligaments being removed to place the prosthesis. To protect the hip from dislocating total hip precautions are instituted post operatively. Positions of hip adduction and hip flexion and internal rotation put the greatest stress on the prosthesis and can result in dislocation posteriorly. (Ref 12).

The vast majority of total hip replacements are successful. (Ref. 7). Complication of total hip replacements do occur, however, and the most common complications are loosening of the prosthesis, dislocation and infection. (Ref 12). Dislocation of the hip is the second most common complication. (Ref. 14). In one study, e.g., approximately 4% of total hip replacements performed using a posterior approach resulted in dislocation. (Ref. 13). Causes of total hip dislocation are surgical factors such as improper placement of the components, patient factors such as poor soft tissue tension and poor patient compliance, or prosthesis factors. (Ref. 13, Ref 15). The patients place the leg in an adducted or leg crossing over position and hyperflexion of the hip. This position places the greatest strain on the hip and leads to dislocation posteriorly or out the back of the acetabular cup. (Ref. 12).

Treatment

Treatment for total hip dislocations includes placing the dislocated femoral head back into the acetabular cup manually under anesthesia. (Ref. 9). The patient is placed in a brace and the hip kept from going into positions that place it at risk of re-dislocating until the soft tissues re-tighten. Once a patient dislocates a total hip replacement, they are at greater risk of re-dislocating in the future. If re-dislocation occurs the replacement and adjustment of component position may be necessary. (Ref. 12). If re-dislocation continues to reoccur then placement of a constrained prosthesis may be necessary. (Ref. 16, Ref. 17). Once total hip dislocations occur there is a risk of multiple surgeries and poorer final functional outcome for the patient. (Ref 12).

Janssen et al. U.S. Pat. No. 4,024,588 describes artificial joints wherein a permanent magnetic field is created between two components for attraction or repulsion by placing permanent magnets in both components of the total joint prosthesis. They specifically demonstrate this for a multitude of joint replacements including total joint replacements in which femoral and acetabular components have magnets. Bertram US. 2003/0236572 further describes total joint replacements using magnetism to control instability. While magnet placements are described in such references which allow translation in various joints while providing increased stability, there is no disclosure regarding placements of magnets of varying strength in joints to decrease risk of dislocation, and in particular to prevent hip dislocations posteriorly, while also reducing the risk of component loosening due to strength of the magnetic fields.

Hyde, Jr. U.S. Pat. Pub. No. 2002/0128651 describes apparatus and methods for stabilizing and/or maintaining adjacent bone portions in predetermined desired relationships and for constraining one, two or three dimensional motion and/or rotation of the adjacent bone portions wherein implanted magnetic arrays provide interacting magnetic fields in the area of the bone portions. While magnet placements are described which generate interacting magnetic fields in an articular joint to reduce the joint reactive forces while constraining the bone portions to move in a natural joint motion, there is again no disclosure regarding placements of magnets in joints to decrease risk of dislocation, and in particular to prevent hip dislocations posteriorly, while also reducing the risk of component loosening due to strength of the magnetic fields.

LIST OF REFERENCES CITED ABOVE

1. Moskowitz, R W, Altman, R D, Hochberg, M C, Buckwalter, J A, Goldberg, V M. Osteoarthritis: Diagnosis and Medical/Surgical Management. $4^{th}$ edition, Lippincott Williams and Wilkins, 2007, pp 2-61.
2. Rogachefsky, R A, Altman, R D, Markov, M M, Cheung, H S. Use of a Permanent Magnetic field to Inhibit the Development of Canine Osteoarthritis. Bioelectromagnetics, Vol 25, May 2004, pp. 260-270.
3. Dahuja, A, Dahuja, G, Walia, J P S. A Prospective Study on the Role of Cemented Total Hip Arthroplasty in Osteonecrosis of the Hip Joint with Femoral Head Collapse in the Elderly: A Study of 100 Cases. Journal of Medical and Dental Science. Vol 6, Issue 5, May-June 2013, pp 57-60.
4. Niebauer, J, King, D. Arthrodesis of the Hip produced by Internal Fixation. J Bone Joint Surg, 28(1) January 1946, pp103-112.
5. Chan, K, Olubimpe, A, McKnight, L, Ignacy, T, Farrokhyar, F, Achilleas, T. Pyrocarbon versus Silicone Proximal Interphalangeal Joint arthroplasty: A Systemic Review. Plastic and Recon Surg, Vol 131(1) January 2013, pp114-124.
6. Georgiades, G, Babis, G C, Hartofilakidis, G. Charnley, J. Low-Friction Arthroplasty in Young Patients with Osteoarthritis. Outcomes at a Minimum of Twenty Two Years/J Bone Joint Surg, Am vol 91, 2009, pp 2846-2851.
7. Keener, J D, Callahan, J J, Goetz, Pederson, D R, Sullivan, P M, Johnston, R C. Twenty-Five-Year Results After Charnley Total Hip Arthroplasty in Patients Less than Fifty Years old. Journ Bone Joint Surg, Vol. 85-A June 2003, 1066-1072
8. Charnley, J. The Long term Results of Low Friction Arthroplasty of the Hip Performed as a Primary Intervention. Journ Bone Joint Surg. Vol 54-B, February 1972, pp 61-76.
9. Daecke, W, Kaszap, B, Martini, A K, Hagena, F W, Rieck, B, Jung, M. A Prospective, Randomized Comparison of 3 Types of Proximal Interphalangeal Joint Arthroplasty. J Hand Surg, Vol 37A, September 2012, pp 1770-1779.
10. McGuire, D T, White, C D, Carter, S L, Solomons, M W. Pyrocarbon Proximal Interphalangeal Joint Arthroplasty: Outcome of a Cohort study. J Hand Surg, Eur, Vol 37, July 2012, pp 490-496.
11. Kim, J M, Chaitayna, S M, Konopka, J, Jupiter, J B. Complications of Total Elbow Arthroplasty. J Am acad Orthoped Surg, vol 19, June 2011, pp. 328-339
12. Woo, R Y, Morrey, B F. Dislocation after Total Hip Arthroplasty. Journal Bone Joint Surg, 64-A, December 1982, pp. 1295-1306.

13. Blom, A W, Rogers, M, Taylor, A H, Patterson, G, Whitehouse, S, Bannister, G C. Dislocation following Total Hip Replacement: Avon Orthopedic Centre Experience. Ann. R Coll Surg Engl, 90(8) November 2008, 658-662.
14. Dewal, H, S E, DiCesare, P E. Instability following Total Hip Arthroplasty. Am J Orthop Aug 2003, 32(8), 377-382
15. Padgett, D E, Warashina, H. The Unstable Total Hip Replacement. Clin Orth Rel Res. March 2004m (420) 72-79.
16. Soong, M, Rubash, H E, Macauley, W. Dislocation after Total Hip Arthroplasty. J Am Acad Orthop Surg. 2004, Sept-Oct: 12(5):314-321
17. Goetz, D D, Capello, W N, Callaghan, J J, Brown, T D, Johnston R C. Salvage of a Recurrently Dislocating Total Hip Prosthesis with Use of a Constrained Acetabular Component. Journal Bone and Joint Surgery. 80-A, April 1998, pp 502-509.

There is a need in the art for an improved joint prosthesis, method for repairing body joints, and joint replacement system for joints that are at risk of dislocation, and in particular for an improved hip prosthesis, method for repairing hip joints, and hip joint replacement systems.

SUMMARY

This disclosure satisfies the foregoing need in the art by providing according to one aspect an improved joint prosthesis comprising first and second articulated corresponding joint components implantable within a body of a patient, wherein the corresponding joint components have corresponding surfaces that are relatively displaceable with respect to each other over a predefined functional range of motion of the corresponding joint components, wherein the corresponding joint components each comprise one or more magnetic elements creating gradient magnetic fields having relatively strongest and weakest field areas over different portions of each of the corresponding surfaces, and wherein the gradient magnetic fields are strongest in attraction at positions of the corresponding surfaces which align when the corresponding surfaces are at a boundary of the predefined functional range of motion, and deter joint dislocation by deterring relative movement of the corresponding surfaces beyond the boundary.

In a particular embodiment, the joint prosthesis is a hip prosthesis comprising a femoral component comprising a femoral head portion having a spherical surface, and an acetabular component having a concave surface corresponding to the spherical surface of the femoral head portion, wherein the spherical surface of the femoral head portion is relatively displaceable with respect to the concave surface of the acetabular component over a predefined functional range of motion of the femoral head portion when positioned within the acetabular component. The spherical surface of the femoral head portion and the concave surface of the acetabular component each comprise designated anterior and posterior surface areas, the femoral head portion comprises one or more permanent magnets positioned to provide a strongest magnetic field over the surface of the femoral head portion at a position corresponding to the anterior surface area of the femoral head portion, and the acetabular component comprises one or more permanent magnets positioned to provide a strongest magnetic field over the concave surface at a position corresponding to the posterior surface area of the acetabular component, wherein the position corresponding to the anterior surface area of the femoral head portion and the position corresponding to the posterior surface area of the acetabular component align at a boundary of the predefined functional range of motion of the femoral head portion within the acetabular component.

In another aspect, a method of repairing a body joint is described comprising securing first and second articulated corresponding joint components to adjacent bones within a body of a patient, wherein the secured corresponding joint components have corresponding surfaces that are relatively displaceable with respect to each other over a predefined functional range of motion of the secured corresponding joint components, wherein the secured corresponding joint components each comprise one or more magnetic elements creating gradient magnetic fields having relatively strongest and weakest field areas over different portions of each of the corresponding surfaces, and wherein the gradient magnetic fields are strongest at positions of the corresponding surfaces which align when the corresponding surfaces of the secured corresponding joint components are at a boundary of the predefined functional range of motion, and deter joint dislocation by deterring relative movement of the corresponding surfaces beyond the boundary.

In a particular embodiment, the joint is a hip joint and the method comprises securing a femoral component to a femur and an acetabular component to a pelvis, wherein the secured femoral component comprises a secured femoral head portion having a spherical surface, and the secured acetabular component has a concave surface corresponding to the spherical surface of the femoral head portion, wherein the spherical surface of the secured femoral head portion is relatively displaceable with respect to the concave surface of the secured acetabular component over a predefined functional range of motion of the secured femoral head portion when positioned within the secured acetabular component. The spherical surface of the secured femoral head portion and the concave surface of the secured acetabular component each comprise anterior and posterior surface areas in relation to their secured positions, the femoral head portion comprises one or more permanent magnets positioned to provide a strongest magnetic field over the surface of the femoral head portion at a position corresponding to the anterior surface area of the secured femoral head portion, and the acetabular component comprises one or more permanent magnets positioned to provide a strongest magnetic field over the concave surface at a position corresponding to the posterior surface area of the secured acetabular component, wherein the position corresponding to the anterior surface area of the secured femoral head portion and the position corresponding to the posterior surface area of the secured acetabular component align at a boundary of the predefined functional range of motion of the secured femoral head portion within the secured acetabular component.

These and other aspects and features of the disclosure will be appreciated with reference to the following detailed description and accompanying figures, in which embodiments of the disclosure are described and illustrated.

DETAILED DESCRIPTION

As used herein, a "magnetic element" generally refers to a component that includes a magnet or that responds to a magnetic field, i.e., by being attracted to or repelled by a magnet.

In accordance with certain embodiments of the disclosure, to avoid the complications of hip dislocations permanent magnets are placed in selected positions of the femoral and acetabular components of a hip prosthesis, where the magnets in the femoral and acetabular components are placed so as to create a more stable connection between the femoral and acetabular components when such components are under greatest strain for causing dislocation of the joint.

Figure 1:
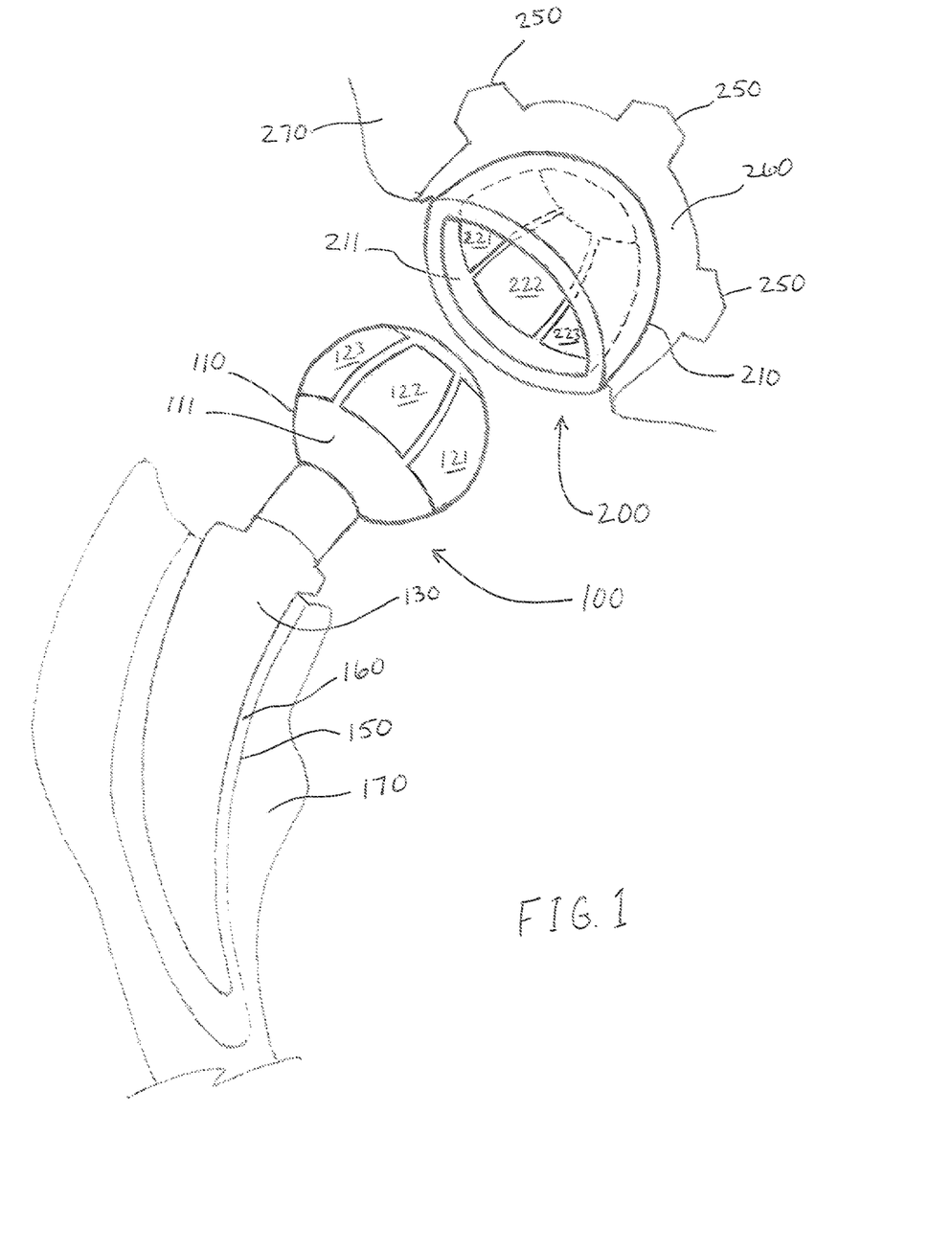
FIG. 1 is a perspective view showing components of a hip replacement joint in accordance with an embodiment of the disclosure, in which portions of the pelvis and femur are also shown.

The present disclosure describes placing permanent magnets in total hip replacements and other joint replacements that are at risk of dislocating, wherein the magnetic arrangement provides a gradient of magnetic field strength in which the highest field strengths of the magnets align at the position of greatest strain and risk for dislocation for that prosthesis. For example, in one embodiment for total hip joint replacements as shown in FIG. 1, femoral component 100 comprises a shaft portion 130 cemented with cement 160 into a recess 150 provided in the femur 170, and a femoral head portion 110 having a generally spherical surface 111. Acetabular component 200 comprises a cup shaped socket portion 210 fixed to the pelvis 270 by cement 260 anchored in bores 250 formed in the pelvis. Socket portion 210 has an inner concave surface generally corresponding to the spherical surface of the femoral head portion, whereby the spherical surface of the femoral head portion is relatively displaceable with respect to the concave surface of the acetabular component over a predefined functional range of motion of the femoral head portion when positioned within the acetabular component. Both femoral head 110 and acetabular socket 210 components have permanent magnets placed in each component to give a more stable connection when they align at a boundary of the predefined functional range of motion. In the depicted embodiment of FIG. 1, one set of magnets 121, 122, 123 of varying strength are placed in the femoral head and a corresponding second set of magnets 221, 222, 223 are placed in the acetabular cup. The permanent magnets are placed in a gradient type fashion. Since the position of greatest risk for dislocation in total hip replacements performed using a posterior approach is flexion greater than 90 degrees, and more particularly a combination of adduction, flexion and internal rotation (Ref 12), the permanent magnets are placed in an arrangement specifically to counteract these forces and reduce the risk of dislocation.

More specifically, the strongest magnets may be placed in a designated or secured anterior surface area of the femoral head portion and a designated or secured posterior surface area of the acetabular component, so that such strongest magnets align at a boundary of a predefined functional range of acceptable relative movement corresponding to flexion up to from about 90-120 degrees (e.g., approximately 100 degrees), where beyond such boundary there is an anticipated unacceptable risk of dislocation. Even more specifically, the strongest magnets may be placed in a designated or secured medial side of the anterior surface area of the femoral head portion and a designated or secured lateral side of the posterior surface area of the acetabular component, so that such strongest magnets align at a boundary of a predefined functional range of acceptable relative movement during combined adduction, flexion and internal rotation, beyond which boundary there is an anticipated unacceptable risk of dislocation. In typical cases, for example, such boundary may be approximated by combined ranges of from 20-30 degrees of adduction, from 90-120 degrees of flexion, and from 20-40 degrees of internal rotation. More specifically, e.g., in one particular embodiment such boundary may be located at a position corresponding to approximately 25 degrees of adduction, 110 degrees of flexion, and 30 degrees of internal rotation.

One or more lower strength magnets may be used in combination with the higher strength magnets, so as to provide a lower level of magnetic strength attraction when the joint is moved in positions where there is less risk of dislocation, while decreasing the risk of component loosening caused by strong magnetic fields over the entire joint surfaces. As shown in FIG. 1, e.g., the femoral component 100 and socket component 200 are depicted showing a generally front view of the right hip, wherein lower strength magnets 222, 223 are placed in the front and mid portion of the acetabulum component, and lower strength magnets 122, 123 are placed in the midportion and posterior aspect of the femoral component. The magnets 121 and 221 with greater strength are placed in the corresponding positions of the acetabular and femoral components that align when the joint has the highest risk of dislocation, which correspond to the anterior aspect of the femoral head and the posterior aspect of the acetabulum (and in one embodiment, more particularly the medial anterior aspect of the femoral head and the lateral posterior aspect of the acetabulum). When the patient extends, abducts and externally rotates the hip, the hip would be in a relatively stable position and the weaker strength magnets on each component would engage. When the prosthesis is placed in a position of greatest strain such as hyperflexion, adduction and internal rotation, the corresponding magnets 121, 221 with the greatest magnetic field strength would engage to provide increased stability at a boundary of a predefined acceptable functional range of motion as described above by counteracting the position of greatest force and strain and deterring movement beyond such boundary to avoid hip dislocation.

The designated anterior and posterior surface areas of the hip joint components are determined in relation to the anticipated physiological placement of the components when secured to the femur and pelvis, and may be uniquely defined by positionally unique anatomical features of the components (e.g., where the components comprise anatomical features designed to be secured in a single unique anatomical orientation, such as, e.g., curve of the femoral stem portion having an attached femoral head to uniquely fit a left or right femur), or by actual designation markings provided on the components specifying which areas should be positioned anteriorly or posteriorly when secured (e.g., where the components may otherwise be secured in a variety of orientations). More particularly, e.g., where an essentially circumferentially symmetric acetabular cup component is employed, one section of the cup surface may be marked as the designated posterior surface (i.e., the surface having the stronger magnet therein), and the surgeon may then accordingly correctly position such component based on such marking. The marking may be in the form of, e.g., alphanumeric characters, color coding, or any other discernable marking system. The components further may advantageously be marked as either left or right components, with designated lateral or medial sides, allowing for the further specific fine placement of gradient magnetic fields aligned laterally or medially in accordance with further specific embodiments.

The magnets positioned in the femoral and acetabular components function as magnetic ligaments providing greater stability to the prosthesis. Range of magnets strength used may be, e.g., from 0.5 gauss to 5000 gauss. One embodiment for example would be placing 100 gauss magnets as magnets 123, 223 at the posterior femoral head and anterior acetabulum; 500 gauss magnets as magnets 122, 222 at the midpoint of the femoral head and corresponding midportion of the acetabulum; and 1250 gauss magnets as magnets 121, 221 at the corresponding anterior aspect of the femoral head and posterior aspect of the acetabulum. This gradient will provide lesser strength magnets aligned at the less strain positions of the total hip replacement, and greater strength magnets aligned at the greater strain positions of the total hip replacement for increased stability when the joint is subject to greater risk of dislocation.

The advantage of this arrangement over use of equally strong magnets to provide a confluent and equal strength magnetic field is that it can decrease the chance of acetabular and/or femoral component loosening from the corresponding bone. Loosening of the acetabular and femoral components is another significant complication of hip arthroplasty (Ref 6). Increased loosening of the components has an even greater probability with longer term follow-up. When acetabular or femoral loosening occurs this leads to pain and the need to revise the components (Ref 6, Ref 7). The use of strong magnetic fields across the entire femoral and acetabular surface would increase the connection between the two components through complete range of motion and increase stress and pull, potentially causing increased incidence of acetabular and femoral component loosening from the acetabular and femoral bone surface. With a gradient magnetic field the highest magnetic field and highest connection would occur between the two components only at the highest strain position of hip flexion, adduction and internal rotation. In the other hip positions there would be a weaker magnetic field connection where dislocation is not at high risk. As a result, there would be less stress overall on the acetabular and femoral components, acetabular and femoral bone interface and decreased chance of loosening.

The magnets described in this disclosure preferably have up to 5000 Gauss surface strength. They may be made from any number of materials, including neodymium, metal alloy, ceramic or rubberized magnetic material.

Figure 2:
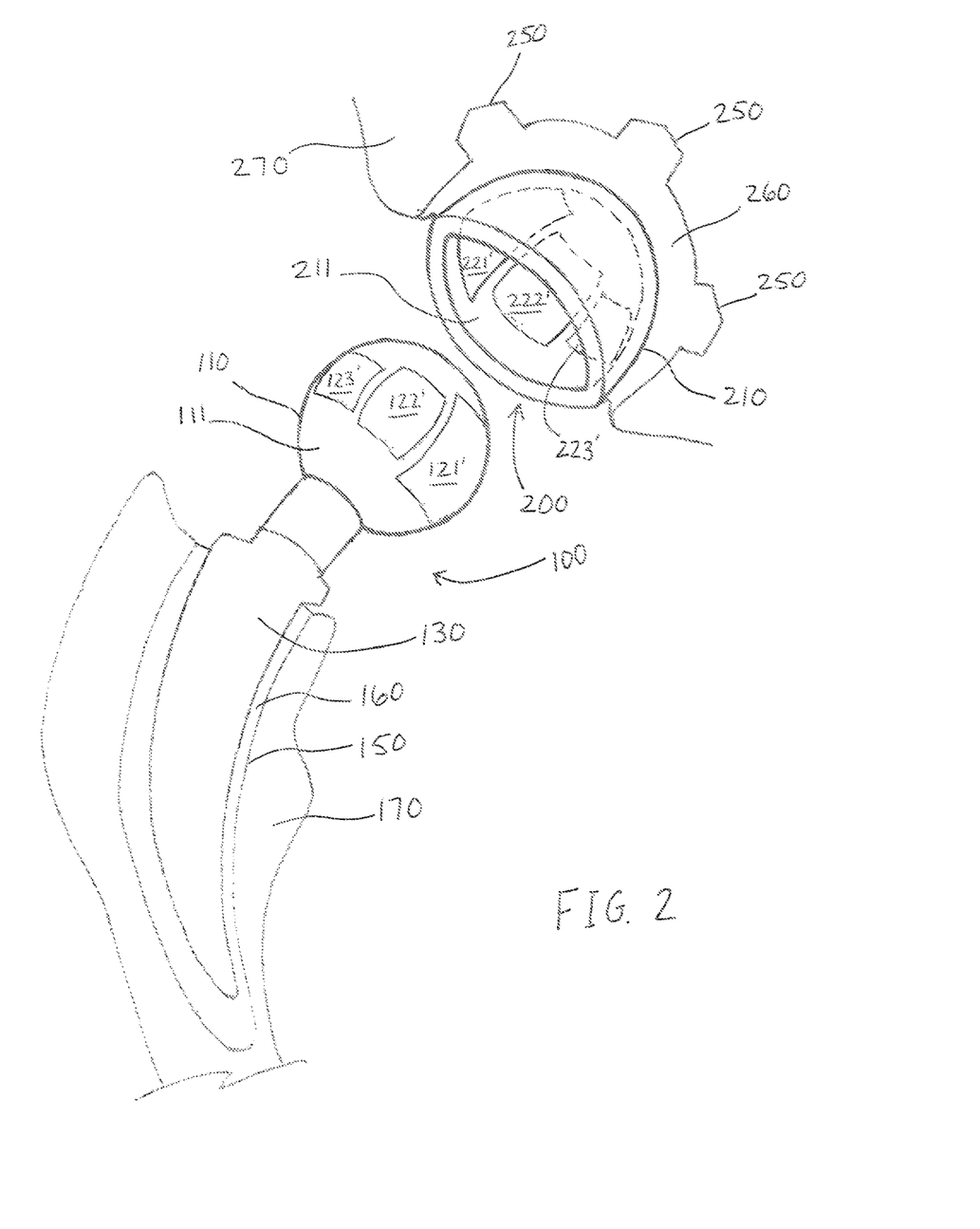
FIG. 2 is a perspective view showing components of a hip replacement joint in accordance with a further embodiment of the disclosure, in which portions of the pelvis and femur are also shown.

Any strength of magnetic field could be used in a gradient type of fashion to increase the connection between the total hip components. Magnets of varying composition and/or size may be employed to provide different magnetic field strengths. For example, where magnets of similar size as shown in FIG. 1 are employed, the compositions of the magnets may be different such that a relatively stronger magnetic material such as NdFeB 48 is employed for magnets 121, 221, while a relatively weaker magnetic material such as NdFeB 33 is employed for magnets 122, 222 and/or 123, 223. Alternatively, as shown in FIG. 2, magnets 121', 221' may be made of similar material as that of 122', 222' and/or 123', 223', but be substantially larger in size to create a relatively stronger magnetic field. While larger surface area magnets are depicted in FIG. 2, thicker magnets may alternatively be employed to create a stronger magnetic field.

In one embodiment the total hip components are made with the permanent magnets premade into the components as in FIGS. 1 and 2. For example, the magnetic elements may be imbedded in a surface of the joint components. In one example, the joint component may include a series of bores or similar cutouts in its surface, each disposed to accept the respective magnetic element. The magnetic elements may be retained in such a bore or opening using any conventional method, including but not limited to adhesive, press fit, and by other mechanical fasteners. In another embodiment, the femoral and acetabular components are premade with openings or slots for the placement of the permanent magnets and the gradient arrangement determined intraoperatively by the surgeon based on the surgeon's preference. A liner of appropriate material (e.g., polyethylene) and thickness may be employed over the magnets to provide desired joint component contact properties while also ensuring that the corresponding magnetic fields interact and attract.

Permanent magnets employed in the disclosure could be made from metal, or ceramic depending on the corresponding total joint replacement material. The permanent magnetic field across the femoral and acetabular component would allow patients greater freedom of motion without the higher probability of dislocation. If the components have to be separated such as if the component or components are being replaced, then the components could be separated from each other by placing a thin material between the two components. The material could be any material that is non-ferrous and can block the magnetic field such as plastic.

In various embodiments, depending upon the strength of the magnets used, the embodiments of the disclosure may further employ a shield that is placed over the magnetic components, i.e., to limit the impact of the magnetic field beyond the inside of the joint. For example, it may be desirable to shield the magnetic components to prevent accidental attraction or repulsion of the magnetic components to metal or magnets in the environment. More particularly, the magnets in the femoral and/or acetabular components of a hip joint further may be shielded on a side thereof directed away from the relatively displaceable corresponding surfaces of the femoral and acetabular components, so as to shield the external environment from the magnetic fields of the magnetic components, while not preventing the desired interaction between the magnetic components. The shielding may be achieved, e.g., by fixing a shielding material to at least one of the femoral and acetabular components to cover at least one side of the magnets. More specifically, the shielding may be achieved by applying a shielding material directly to at least one surface of a magnet. Shielding may be especially useful, e.g., when using magnets in more superficial joints such as finger, wrist, ankle, etc.

By using a gradient magnetic field to selectively positionally attract components and thereby forming magnetic ligaments at specific position alignments when dislocation is at risk, greater stability is imparted for the prosthesis. By providing greater stability the probability of dislocation of the prosthesis decreases and functional range of motion is improved.

In still other embodiments of the disclosure, it may be desirable that the respective joint components further include magnetic elements which repel each other, which may align during joint movements between the boundaries of the predetermined functional range of motion where dislocation is not at high risk, so as to reduce wear and tear on the joint components during such movements where dislocation is not at high risk, while still providing alignment of strongest attracting magnets at the boundary of the predefined functional range of motion where dislocation is at risk.

The disclosure further relates to a method of repairing a body joint comprising securing first and second articulated corresponding joint components to adjacent bones within a body of a patient, wherein the secured corresponding joint components have corresponding surfaces that are relatively displaceable with respect to each other over a predefined functional range of motion of the secured corresponding joint components, wherein the secured corresponding joint components each comprise one or more magnetic elements creating gradient magnetic fields having relatively strongest and weakest field areas over different portions of each of the corresponding surfaces, and wherein the gradient magnetic fields are strongest at positions of the corresponding surfaces which align when the corresponding surfaces of the secured corresponding joint components are at a boundary of the predefined functional range of motion, and deter joint dislocation by deterring relative movement of the corresponding surfaces beyond the boundary.

In practice, the joint components could be attached to the bone using any known method including adhesive or mechanical fastener, cement or screw. As will be appreciated by those of ordinary skill in the art, the surface of the respective bone to which each of the joint components is attached may require some preparation prior to attachment. For example, each of the bone surfaces to which the joint components are attached may need to be stripped of any ligament. Moreover, degenerated cartilage and bone material may necessarily be removed from the bone.

In a more particular embodiment, the joint is a hip joint and the method comprises securing a femoral component to a femur and an acetabular component to a pelvis, wherein the secured femoral component comprises a secured femoral head portion having a spherical surface, and the secured acetabular component has a concave surface corresponding to the spherical surface of the femoral head portion, wherein the spherical surface of the secured femoral head portion is relatively displaceable with respect to the concave surface of the secured acetabular component over a predefined functional range of motion of the secured femoral head portion when positioned within the secured acetabular component. In even more specific embodiments, the spherical surface of the secured femoral head portion and the concave surface of the secured acetabular component each comprise an anterior surface area and a posterior surface area, the femoral head portion comprises one or more permanent magnets positioned to provide a strongest magnetic field over the surface of the femoral head portion at a position corresponding to the anterior surface area of the secured femoral head portion, and the acetabular component comprises one or more permanent magnets positioned to provide a strongest magnetic field over the concave surface at a position corresponding to the posterior surface area of the secured acetabular component, wherein the position corresponding to the anterior surface area of the secured femoral head portion and the position corresponding to the posterior surface area of the secured acetabular component align at a boundary of the predefined functional range of motion of the secured femoral head portion within the secured acetabular component.

According to the embodiments just described, the functionality of the joint after inserting the prosthesis is substantially the same as prior to surgery. The joint components move relative to each other in a sliding engagement, as necessary, recreating the normal kinematics of the joint.

Although the disclosure has been primarily described in terms of replacing a hip joint, and more particularly with regard to deterring hip dislocation posteriorly at the highest strain position of hip flexion, adduction and internal rotation which may be most beneficial when the hip replacement procedure is performed using a posterior approach compromising the posterior capsule and ligaments, it may be used in other instances. Specifically, the novel concepts described herein may be employed to prevent other forms of potential hip dislocations at other boundaries of predefined functional ranges of motion, such as anterior dislocations, which while less likely to occur may be of concern such as when the hip replacement is performed using an alternative anterior approach. In such instance, the relatively stronger magnets may alternatively be positioned to align when the spherical surface of the femoral head portion and the concave surface of the acetabular component reach a position of strain associated with potential anterior dislocation. Additionally, the novel concepts described herein may further be used in other instances of joints that include bones that move relatively and are prone to dislocation at certain positions. Other joints that are replaced include total knee replacements, total elbow replacements, total ankle replacements, total shoulder replacements, total wrist replacements and finger replacements. (Ref 5, Ref 9, Ref. 10, Ref. 11) For example, non-constrained proximal interphalangeal joint and metacarpal phalangeal joint implants have a risk of dislocation over time. (Ref 9, Ref. 10) This situation especially occurs when pyrocarbon implants are used or when the soft tissues are more compromised such as rheumatoid arthritis. (Ref. 9) For conventional shoulder joint prostheses (maintaining a spherical humeral head component and a recessed cup-shaped glenoid component), dislocation is usually more prone to be anterior as a result of external rotation and abduction. Accordingly, different strength magnets may be used in such conventional shoulder prostheses components such that the strongest magnetic fields align upon external rotation and abduction. For reverse shoulder prostheses (where the glenoid component is provided with a spherical ball-like surface and the humeral head is provided with a recessed cup-shaped surface), however, posterior dislocation may be more likely upon adduction, flexion and internal rotation. Accordingly, different strength magnets may be used in such reverse shoulder prostheses components such that the strongest magnetic fields align upon adduction, flexion and internal rotation.

The disclosure also is not limited to application in humans. Those having ordinary skill in the art will appreciate many additional applications, such as in animal applications.

While the invention has been described in connection with several presently preferred embodiments thereof, those skilled in the art will appreciate that many modifications and changes may be made without departing from the true spirit and scope of the invention which accordingly is intended to be defined solely by the appended claims.

The invention claimed is:

1. A hip joint prosthesis, comprising:
a femoral head comprising a plurality of magnets positioned on an anterior surface of the femoral head, the plurality of magnets comprising a first femoral magnet and a second femoral magnet, the first femoral magnet configured to provide a stronger magnetic field than the second femoral magnet;
an acetabular cup corresponding to the femoral head, the acetabular cup comprising a second plurality of magnets positioned on a posterior surface of the acetabular cup, the second plurality of magnets comprising a first acetabular cup magnet and a second acetabular cup magnet, the first acetabular cup magnet configured to provide a stronger magnetic field than the second acetabular cup magnet;

wherein the femoral head is configured to rotate within the acetabular cup through a range of motion corresponding to about 0-120 degrees of hip flexion, the first femoral magnet positioned on a medial side of the anterior surface of the femoral head and the first acetabular cup magnet positioned on a lateral side of the posterior surface of the acetabular cup such that the first femoral magnet and the first acetabular cup magnet align to form the strongest magnetic force between the first femoral magnet and the first acetabular cup magnet when the femoral head is in a position corresponding to about 90-120 degrees of hip flexion.

2. The hip joint prosthesis of claim 1, wherein the first femoral magnet and the second femoral magnet comprise permanent magnets of varying size or thickness positioned to provide a varying magnetic field over the surface of the femoral head or over the surface of the acetabular cup.

3. The hip joint prosthesis of claim 2, wherein the permanent magnets have gauss strengths within the range of from 0.5-5000 gauss.

4. The hip joint prosthesis of claim 1, wherein the first femoral magnet and the first acetabular cup magnet align when the femoral head is located at a position corresponding to about 20-30 degrees of hip adduction and from about 20-40 degrees of hip internal rotation.

5. The hip joint prosthesis of claim 4, the position corresponds to approximately 25 degrees of hip adduction, 110 degrees of hip flexion, and 30 degrees of hip internal rotation.

6. The hip joint prosthesis of claim 1, wherein the femoral head and the acetabular cup have openings for placement of the magnets.

7. The hip joint prosthesis of claim 6, further comprising a lining placed over the openings, wherein the lining forms at least a portion of the femoral head or the acetabular cup.

8. The hip joint prosthesis of claim 7, wherein the lining comprises a biocompatible material with a low coefficient of friction.

9. The hip joint prosthesis of claim 8, wherein the lining is made of one of polyethylene, ceramic, and pyrolytic carbon.

10. The hip joint prosthesis of claim 1, wherein at least one of the femoral head and the acetabular cup comprise magnetic field shielding.

11. The hip joint prosthesis of claim 1, wherein the first femoral magnet is constructed from a first material and the second femoral magnet is constructed from a second material.

12. The hip joint prosthesis of claim 11, wherein the first acetabular cup magnet is constructed from the first material and the second acetabular cup magnet is constructed from the second material.

13. A hip joint prosthesis, comprising:
a femoral head comprising a plurality of magnets positioned on an anterior surface of the femoral head, the plurality of magnets comprising a first femoral magnet and a second femoral magnet, the first femoral magnet configured to provide a stronger magnetic field than the second femoral magnet;
an acetabular cup corresponding to the femoral head, the acetabular cup comprising a second plurality of magnets positioned on a posterior surface of the acetabular cup, the second plurality of magnets comprising a first acetabular cup magnet and a second acetabular cup magnet, the first acetabular cup magnet configured to provide a stronger magnetic field than the second acetabular cup magnet;
wherein the femoral head is configured to rotate within the acetabular cup through a range of motion corresponding to about 0-120 degrees of hip flexion, the first femoral magnet positioned on a medial side of the anterior surface of the femoral head and the first acetabular cup magnet positioned on a lateral side of the posterior surface of the acetabular cup such that the first femoral magnet and the first acetabular cup magnet align to form the shortest distance between the first femoral magnet and the first acetabular cup magnet when the femoral head is in a position corresponding to about 90-120 degrees of hip flexion.

* * * * *